United States Patent [19]

Withycombe et al.

[11] 4,207,905

[45] Jun. 17, 1980

[54] ISOBUTYL SUBSTITUTED HETEROCYCLIC COMPOUNDS FOR AUGMENTING OR ENHANCING THE ORGANOLEPTIC PROPERTIES OF SMOKING TOBACCOS AND SMOKING TOBACCO ARTICLES

[75] Inventors: Donald A. Withycombe, Lincroft; Braja D. Mookherjee, Holmdel; Manfred H. Vock, Locust; Joaquin F. Vinals, Red Bank, all of N.J.

[73] Assignee: International Flavors & Fragrances Inc., New York, N.Y.

[21] Appl. No.: 887,627

[22] Filed: Mar. 17, 1978

Related U.S. Application Data

[62] Division of Ser. No. 807,056, Jun. 16, 1977, Pat. No. 4,093,752.

[51] Int. Cl.$^2$ .............................................. A24B 3/12
[52] U.S. Cl. .................................. 131/17 R; 131/144
[58] Field of Search ............... 131/2, 17 R, 144, 15 R; 426/536, 537; 260/340.6, 307 F

[56] References Cited
U.S. PATENT DOCUMENTS 3,769,293  10/1973  Hetzel et al. ........................ 260/307

Primary Examiner—Vincent Millin
Attorney, Agent, or Firm—Arthur L. Liberman; Franklin D. Wolffe

[57] ABSTRACT

Processes and compositions are described for the use in smoking tobacco flavor and aroma augmenting, modifying, enhancing and imparting compositions and as smoking tobacco aroma or flavor imparting, augmenting or enhancing materials of a mixture of compounds having the generic structure:

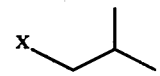

wherein X is a moiety selected from the group consisting of:

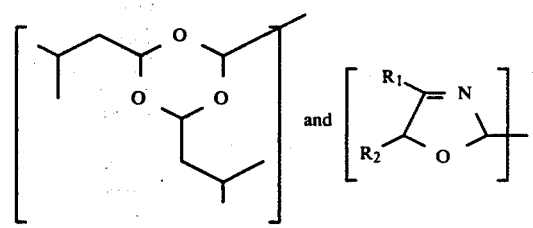

and wherein $R_1$ and $R_2$ are different, one of $R_1$ or $R_2$ being methyl, and the other of $R_1$ or $R_2$ being ethyl, or mixtures of same, including (i) 2,4,6-triisobutyl-1,3,5-trioxane and (ii) 2-isobutyl dialkyloxazolines.

2 Claims, 9 Drawing Figures

NMR SPECTRUM FOR EXAMPLE I
SOLVENT: CDCl$_3$
SWEEP WIDTH: 1000 Hz.

NMR SPECTRUM FOR EXAMPLE I

IR SPECTRUM FOR EXAMPLE I

MASS SPECTRUM FOR EXAMPLE I

NMR SPECTRUM FOR EXAMPLE I
SOLVENT: CDCl$_3$
SWEEP WIDTH: 1500 Hz.

IR SPECTRUM FOR EXAMPLE I

MASS SPECTRUM FOR EXAMPLE I

NMR SPECTRUM FOR EXAMPLE I

IR SPECTRUM FOR EXAMPLE I

ISOBUTYL SUBSTITUTED HETEROCYCLIC COMPOUNDS FOR AUGMENTING OR ENHANCING THE ORGANOLEPTIC PROPERTIES OF SMOKING TOBACCOS AND SMOKING TOBACCO ARTICLES

This application is a divisional of application for United States Letters Patent Ser. No. 807,056, June 16, 1977, now U.S. Pat. No. 4,093,752, issued on June 6, 1978.

BACKGROUND OF THE INVENTION

The present invention relates to a genus of compounds having the generic structure:

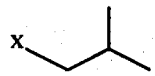

wherein X is a moiety selected from the group consisting of

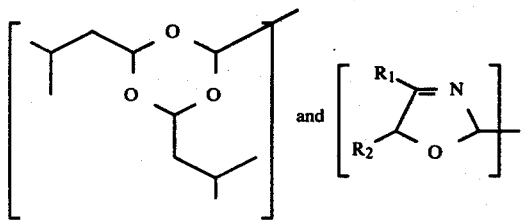

and wherein $R_1$ and $R_2$ are different, one of $R_1$ or $R_2$ being methyl, and the other of $R_1$ or $R_2$ being ethyl, or mixtures of same, and novel compositions using members of such genus of compounds or mixtures of same to augment, modify or enhance the flavor and/or aroma of consumable materials or impart flavor and/or aroma to consumable materials.

There has been considerable work performed relating to substances which can be used to impart (modify, augment or enhance) flavors and aromas to (or in) various consumable materials such as foodstuffs having chocolate, cocoa butter, milk, vanilla, blackberry, cooked vegetable, stew, cooked green vegetable and baked goods flavors and tobaccos which have been produced from reconstituted tobacco having imparted thereto distinctive, pleasing chocolate flavor nuances, or tobaccos having nutty, green and burnt roasted flavor and aroma chatacteristics prior to and on smoking. These substances are used to diminish the use of natural materials, some of which may be in short supply, and to provide more uniform properties in the finished product.

Sweet, dairy-like, creamy, vanilla, berry, milk chocolate-like, chocolate, green pepper, cooked green pepper, spicey, peppery, meaty, roasted, and cocoa butter-like aromas as well as sweet, dairy-like, creamy, vanilla, berry, milk chocolate, green pepper, cooked green pepper, nutty, spicey, peppery, meaty, roasted, chocolate and cocoa butter-like flavor characteristics are particularly desirable for many uses in foodstuff flavors, chewing gum flavors, toothpaste flavors, and medicinal product flavors.

Chocolate-like aromas with cocoa-like and sweet, creamy nuances or nutty, green, burnt roasted aromas prior to smoking, and chocolate-like aroma notes and more tobacco-like smoke aroma characteristics in the main stream and side stream on smoking are desirable in tobaccos and in tobacco flavoring compositions.

German Auslegschrift No. 2,402,416 discloses a sublimable performed composition in tablet form containing 1,3,5-triisopropyl-s-trioxane or 1,3,5-tri-t-butyl-s-trioxane as an active agent whereby the composition may be used to deodorize toilets, telephone mouthpieces, or give off insecticides.

2,4,6-Tri-s-butyl-1,3,5-trioxane is disclosed at Volume 19, page 391 of Beilstein; and it is further disclosed to be a "trimer" of methyl ethyl acetaldehyde (2-methyl butanal). An additional disclosure in Beilstein is at Volume 19, supplement 2 at page 403. Neither Beilstein reference discloses the organoleptic qualities of 2,4,6-triisobutyl-1,3,5-trioxane.

Indeed, the 1,3,5-triisopropyl-s-trioxane has little, if any, aroma or flavor to be of value in flavoring foodstuffs or tobaccos. It is, accordingly, quite surprising that the next adjacent methyl homologue, 2,4,6-triisobutyl-1,3,5-trioxane, has such intense aroma and flavor nuances as described herein.

Trialkyl substituted oxazolines are described in the prior art as being useful for modifying fish flavors in U.S. Pat. No. 3,627,540 issued on Dec. 14, 1971. More specifically, it is stated at Column 2, lines 12–27:

The seafood flavor characteristic of the pentadienal can further be varied by including one or more cyclic oxazo compounds, particularly $\Delta^3$-oxazolines having the formula

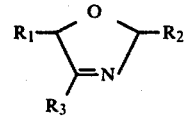

wherein $R_1$, $R_2$ and $R_3$ are hydrogen, alkyl, or alkylene and can be the same or different. It is preferred in certain embodiments of the present invention to use lower alkyl derivatives of oxazoline, preferably those having up to about three carbon atoms in the alkyl group or groups. A preferred oxazoline in certain embodiments of the invention is 2,4,5-trimethyl-$\Delta^3$-oxazoline. U.S. Pat. No. 3,627,540 does not imply, however, that the higher alkyl oxazoline analogue of the instant invention taken alone or in admixture with the 2,4,6-triisobutyl-1,3,5-trioxane of our invention, have flavor and aroma nuances of such quality and intensity as described herein.

Mussinan et al, "Identification and Flavor Properties of Some 3-Oxazolines and 3-Thiazolines Isolated from Cooked Beef," Abstracts of Papers, 170th Meeting, American Chemical Society, August 24–29, 1975, Port City Press, Baltimore, Maryland, Item No. AGFD 022, states:

[22.]IDENTIFICATION AND FLAVOR PROPERTIES OF SOME 3-OXAZOLINES AND 3-THIAZOLINES ISOLATED FROM COOKED BEEF. Cynthia J. Mussinan, Richard A. Wilson, Ira Katz, Anne Sanderson, and Manfred H, Vock. International Flavors and Fragrances, Inc., 1515 Highway 36, Union Beach, New Jersey 07735.

Four 3-oxazolines and two 3-thiazolines have been isolated from beef cooked in a sealed stainless steel vessel at 162.7° and 182°. The compounds were identified by matching retention times and mass spectra with those of authentic compounds synthesized in our laboratory. The compounds identified were 2,4-dimethyl-3-oxazoline; 2,4,5-trimethyl-3-oxazoline; 2,4-dimethyl-5-ethyl-3-oxazoline; 2,5-dimethyl-4-ethyl-3-oxazoline; 2,4-dimethyl-3-thiazoline; and 2,4,5-trimethyl-3-thiazoline. The synthesis, spectra and flavor properties of these and some related compounds will be discussed. None of the oxazoline compounds of Mussinan et al. have properties even remotely similar to those of the compounds containing the oxazoline moieties of the instant invention. Thus, the compounds containing the oxazoline moieties of the instant invention have unexpected, unobvious and advantageous properties with respect to their organoleptic characteristics when compared with the oxazolines of Mussinan et al. and U.S. Pat. No. 3,627,540.

THE INVENTION

Figure 1:
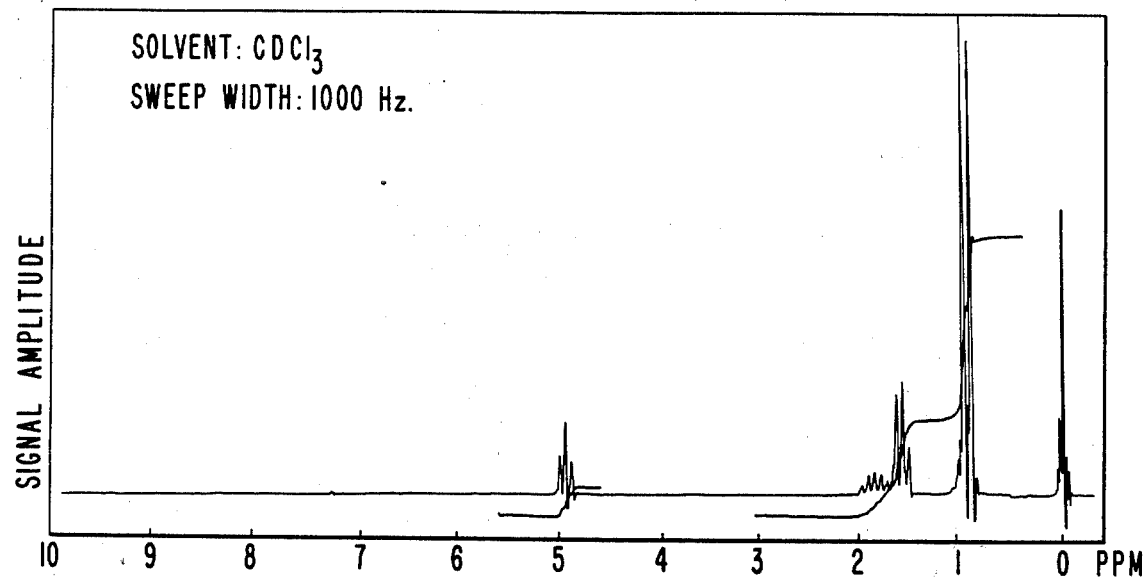
FIG. 1 represents the NMR spectrum for 2,4,6-triisobutyl-1,3,5-trioxane produced according to Example I.

It has now been discovered that novel solid and liquid foodstuff, chewing gum, medicinal product and toothpaste compositions and flavoring compositions therefor having sweet, dairy-like, creamy, vanilla, berry, milk chocolate-like, chocolate, green pepper, cooked green pepper, spicey, peppery, meaty, roasted and cocoa butter-like aromas and sweet, dairy-like, creamy, vanilla, berry, milk chocolate-like, green pepper, cooked green pepper, nutty, spicey, peppery, meaty, roasted, chocolate, and cocoa butter-like flavor characteristics; as well as novel tobacco and tobacco flavoring compositions having chocolate-like, cocoa-like, nutty, green, burnt roasted, and sweet, creamy aromas prior to smoking and chocolate-like aroma notes and more tobacco-like aroma notes on smoking in the main stream and in the side stream may be provided by the utilization of a genus of compounds having the generic structure:

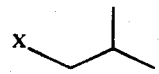

wherein X is a moiety selected from the group consisting of

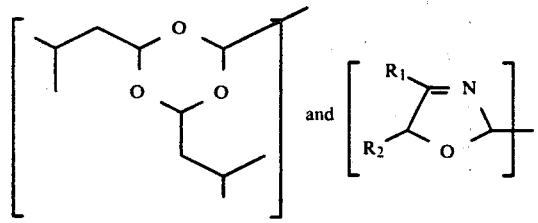

wherein $R_1$ and $R_2$ are different and each is selected from the group consisting of ethyl and methyl or mixtures of same, that is (i) 2,4,6-triisobutyl-1,3,5-trioxane having the structure:

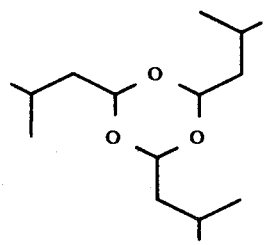

(ii) 2-isobutyl dialkyl oxazolines having the generic structure:

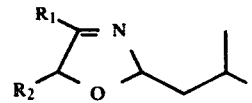

wherein $R_1$ and $R_2$ are different and are each selected from the group consisting of methyl and ethyl or (iii) mixtures of said trioxane and one or more of said oxazolines in foodstuffs, chewing gums, toothpastes, medicinal products, and tobaccos as well as tobacco substitutes.

2,4,6-Triisobutyl-1,3,5-trioxane useful as indicated supra, may be produced, preferably, by one of several processes.

A preferred process comprises the trimerization of isovaleraldehyde in the presence of an acidic catalyst.

More specifically, this process comprises the reaction step:

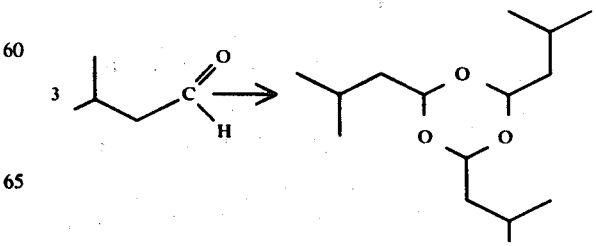

This reaction takes place in the presence of a mineral acid catalyst such as concentrated sulfuric acid or concentrated phosphoric acid. The reaction also takes place in the presence of an inert solvent such as benzene, toluene or xylene. The weight ratio of isovaleraldehyde:solvent may vary from 0.5:1 up to about 5:1 with a preferable weight ratio of about 2:1. The percentage of concentrated acid catalyst in the reaction mass may vary from 0.5% by weight of acid catalyst based on isovaleraldehyde up to 4% by weight of acid catalyst based on isovaleraldehyde. The reaction temperature may vary from about 0° C. up to about 25° C. with a preferable reaction temperature range of from about 5° C. up to about 12° C.

The reaction time is preferably in the range of from 15 hours up to 30 hours.

At the end of the reaction the acidic catalyst is neutralized with base such as sodium hydroxide, potassium hydroxide, sodium carbonate or potassium carbonate. The reaction mass is then washed to neutral with water, and the resultant product is distilled. 2,4,6-Triisobutyl-1,3,5-trioxane may be distilled at 95° C. and 1 mm Hg pressure without any decomposition of the resultant product.

The genus of compounds having the generic structure:

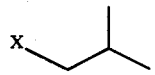

wherein X is one of the moieties selected from the group consisting of

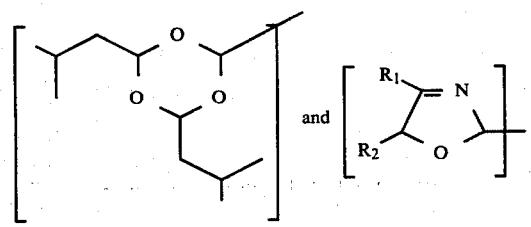

and wherein R₁ and R₂ are different and each is selected from the group consisting of methyl and ethyl, is prepared by a novel process which involves first reacting isovaleraldehyde with aqueous ammonia to form the isovaleraldehyde imine and then reacting the resulting isovaleraldehyde imine with 2(3)-hydroxy-3(2)-pentanone to form the mixture of oxazolines as well as 2,4,6-triisobutyl-1,3,5-trioxane according to the following reaction sequence:

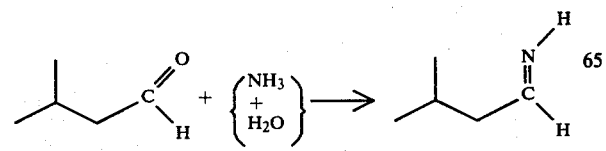

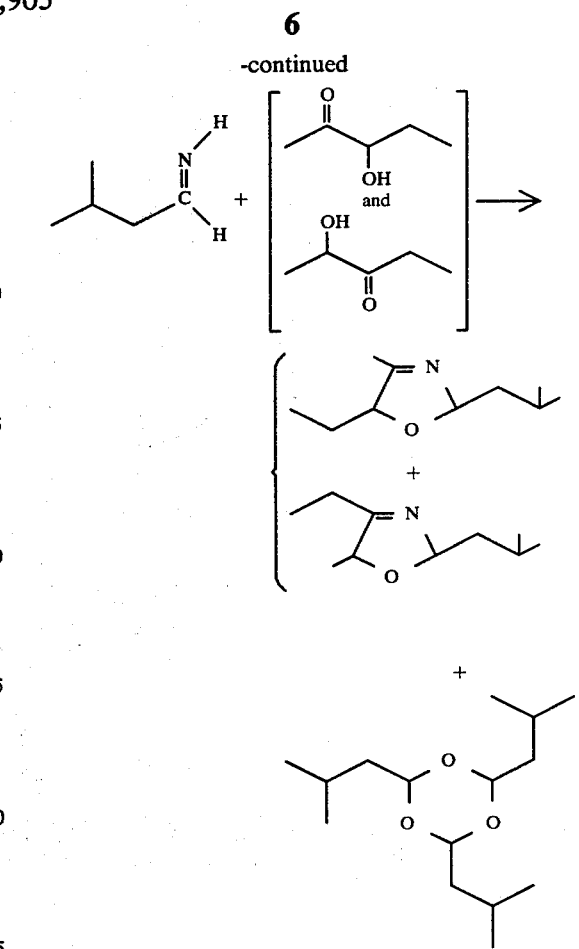

The first reaction, that of aqueous ammonia with isovaleraldehyde, preferably takes place at a temperature in the range of from about 0° C. up to about 10° C. It is most convenient and most preferable to carry out the reaction using a mole ratio of ammonia:isovaleraldehyde of 1:1 although mole ratios of from 0.5:1 up to 2:1 of isovaleraldehyde:ammonia may be used.

The resulting imine may then be reacted with either 2-hydroxy-3-pentanone or 3-hydroxy-2-pentanone or a mixture thereof. This reaction preferably takes place at a temperature in the range of from about 30° C. up to about 50° C. with a preferable temperature range of from 35° up to 40° C. The time of reaction varies with the temperature with the shorter times of reaction being satisfactory if greater temperatures of reaction are used. The most preferred time of reaction is 2 hours using a temperature of from 35°–40° C., but times of reaction of from 1 up to 10 hours are useful.

At the end of the second reaction wherein the oxazolines are formed, the reaction mass is extracted with an inert solvent such as diethyl ether, the organic extract is evaporated and the resulting material is distilled. Preparative GLC may then be used in order to separate the oxazolines from the 2,4,6-triisobutyl-1,3,5-trioxane.

The compounds having the generic structure:

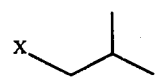

wherein X is:

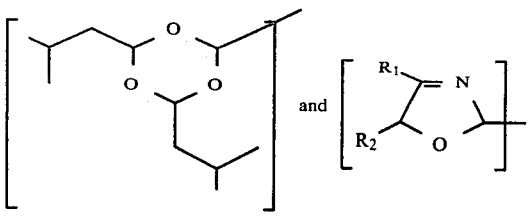

and wherein $R_1$ and $R_2$ are different and each represents ethyl or methyl, that is the compounds (i) 2,4,6-triisobutyl-1,3,5-trioxane, or (ii) 2-isobutyl dialkyl oxazolines or (iii) mixtures of said trioxane and said oxazolines, having the following organoleptic properties:

Table I

| Name of Compound | Structure | Organoleptic Properties as Food Flavor | Organoleptic Properties as Tobacco Flavor |
|---|---|---|---|
| 2,4,6-triisobutyl-1,3,5-trioxane | 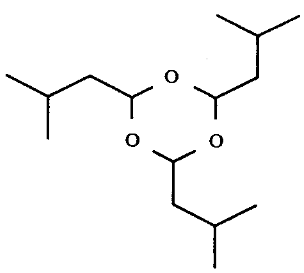 | Sweet, dairy-like, creamy, vanilla, berry-like, milk chocolate-like and cocoa butter-like aroma and a sweet, dairy-like, creamy, vanilla, berry, milk chocolate-like and cocoa butter-like flavor at 15 ppm | A chocolate-like, cocoa-like and sweet, creamy aroma and flavor prior to smoking and a chocolate-like aroma and more tobacco-like nuances on smoking in the main stream and side stream. |
| 5-ethyl-2-isobutyl-4-methyl-3-oxazoline | 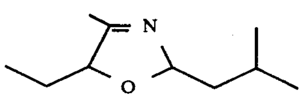 | Cooked green pepper, spicey, peppery and meaty aroma with cooked green pepper, spicey, peppery and meaty flavor characteristics at 10 ppm. | Green pepper-like and slight vegetable-like aroma characteristics prior to and on smoking in the main stream and the side stream. |
| 4-ethyl-2-isobutyl-5-methyl-3-oxazoline | 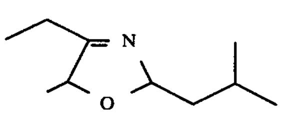 | Green pepper, chocolate and roasted aroma characteristic with green pepper, hydrolyzed vegetable protein mouthfeel, and chocolate, nutty, and roasted notes at 6 ppm. | Chocolate-like, nutty, green, burnt roasted-like aroma prior to smoking and on smoking in the main stream and in the side stream. |

When the isobutyl substituted heterocyclic compounds and/or mixtures of same of our invention are used as a food flavor adjuvant, the nature of the co-ingredients included with the said isobutyl substituted heterocyclic compounds and/or mixtures of same in formulating the product composition will also serve to alter, modify, augment or enhance the organoleptic characteristics of the ultimate foodstuff treated therewith.

As used herein in regard to flavors, the terms "alter", "modify" and "augment" in their various forms mean "supplying or imparting flavor character or note to otherwise bland, relatively tasteless substances or augmenting the existing flavor characteristic where a natural flavor is deficient in some regard or supplementing the existing flavor impression to modify its quality, character or taste".

The term "enhance" is used herein to mean the intensification of a flavor or aroma characteristic or note without the modification of the quality thereof. Thus, "enhancement" of a flavor or aroma means that the enhancement agent does not add any additional flavor note.

As used herein, the term "foodstuff" includes both solid and liquid ingestible materials which usually do, but need not, have nutritional value. Thus, foodstuffs include soaps, convenience foods, beverages, dairy products, candies, vegetables, cereals, soft drinks, snacks and the like.

As used herein, the term "medicinal product" includes both solids and liquids which are ingestible non-toxic materials which have medicinal value such as cough syrups, cough drops, aspirin and chewable medicinal tablets.

The term "chewing gum" is intended to mean a composition which comprises a substantially water-insoluble, chewable plastic gum base such as chicle, or substitutes therefor, including jelutong, guttakay, rubber or certain comestible natural or synthetic resins or waxes. Incorporated with the gum base in admixture therewith may be plasticizers or softening agents, e.g., glycerine; and a flavoring composition which incorporates one or more of the enol esters of our invention, and in addition, sweetening agents which may be sugars, including sucrose or dextrose and/or artificial sweeteners such as cyclamates or saccharin. Other optional ingredients may also be present.

Substances suitable for use herein as co-ingredients or flavoring adjuvants are well known in the art for such use, being extensively described in the relevant literature. It is a requirement that any such material be "ingestibly" acceptable and thus non-toxic and otherwise non-deleterious particularly from an organoleptic standpoint whereby the ultimate flavor and/or aroma of the consumable material used is not caused to have unacceptable aroma and taste nuances. Such materials may in general be characterized as flavoring adjuvants or vehicles comprising broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxy-anisole (mixture of 2- and 3-tertiary-butyl-4-hydroxy-anisole), butylated hydroxy toluene (2,6-di-tertiary-butyl-4-methyl phenol), propyl gallate and the like and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials; lipids; carbohydrates; starches, pectins, and emulsifiers, e.g., mono- and diglycerides of fatty acids, skim milk powder, hexoses, pentoses, disaccharides, e.g., sucrose corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, 2-methyl-2-pentenoic acid, and 2-methyl-cis-3-pentenoic acid; ketones and aldehydes, e.g., acetaldehyde, acetophenone, acetone, acetyl methyl carbinol, acrolein, n-butanal, crotonal, diacetyl, 2-methyl butanal, beta,beta-dimethyl-acrolein, methyl-n-amyl ketone, n-hexanal, 2-hexenal, iso-pentanal, hydrocinnamic aldehyde, cis-3-hexenal, 2-heptanal, nonyl aldehyde, 2-phenyl-2-butenal, 4-methyl-2-phenyl-2-pentenal, 5-methyl-2-phenyl-2-hexenal, 4-(p-hydroxyphenyl)-2-butanone, alpha-ionone, beta-ionone, 2-methyl-3-butanone, benzaldehyde, damascone, damascenone, 2-heptanone, o-hydroxyacetophenone, 2-methyl-2-hepten-6-one, 2-octanone, 2-undecanone, 3-phenyl-4-pentenal, 2-phenyl-4-pentenal, 2-phenyl-2-hexenal, 2-phenyl-2-pentenal, furfural, 5-methyl-furfural, cinnamaldehyde, isovaleraldehyde beta-cyclohomocitral, 2-pentanone, 2-pentenal and propanal; alcohols such as 1-butanol, benzyl alcohol, 1-borneol, trans-2-buten-1-ol, ethanol, geraniol, 1-hexanol, 2-heptanol, trans-2-hexenol-1, cis-3-hexen-1-ol, 3-methyl-3-buten-1-ol, 1-pentanol, 1-penten-3-ol, p-hydroxyphenyl-2-ethanol, isoamyl alcohol, iso-fenchyl alcohol, 2-phenylethanol, alpha-terpineol, cis-terpineol hydrate, eugenol, linalool, acetoin; esters, such as butyl acetate, ethyl acetate, ethyl acetoacetate, ethyl benzoate, ethyl butyrate, ethyl caprate, ethyl caproate, ethyl caprylate, ethyl cinnamate, ethyl crotonate, ethyl formate, ethyl isobutyrate, ethyl isovalerate, ethyl laurate, ethyl myristate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate and terpenyl acetate; hydrocarbons such as dimethyl naphthalene, dodecane, methyl diphenyl, methyl naphthalene, myrcene, naphthalene, octadecane, tetradecane, tetramethyl naphthalene, tridecane, trimethyl naphthalene, undecane, caryophyllene, 1-phellandrene, p-cymene, 1-alphapinene; pyrazines such as 2-methoxy-3-isobutyl pyrazine, 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, methyl ethylpyrazine, tetramethylpyrazine, trimethylpyrazine; essential oils, such as jasmine absolute, cassia oil, cinnamon bark oil, rose absolute, orris absolute, lemon essential oil, Bulgarian rose, yara yara and vanilla; thiazoles such as those set forth in U.S. Pat. No. 3,769,040 including 2,4,5-trimethylthiazole, 2-methyl-5-methoxy-4-isobutylthiazole, 2,4-dimethyl-5-acetylthiazole and 2,4-dimethyl-5-ethylthiazole; thiazolines such as those set forth in U.S. Pat. No. 3,816,445 including 2(2-methylthioethyl)-$\Delta^3$-thiazoline, 2-secondary butyl-$\Delta^3$-thiazoline; 2-n-butyl-$\Delta^3$-thiazoline, 2-isobutyl-$\Delta^3$-thiazoline, 2-pentyl-$\Delta^3$-thiazoline, 2-hexyl-$\Delta^3$-thiazoline and 2-benzyl-$\Delta^3$-thiazoline; lactones such as $\gamma$-nonalactone; sulfides, e.g., methyl sulfide and other materials such as maltol, acetoin and acetals (e.g., 1,1-diethoxy-ethane, 1,1-dimethoxy-ethane and dimethoxymethane).

The specific flavoring adjuvant selected for use may be either solid or liquid depending upon the desired physical form of the ultimate product, i.e., foodstuff, whether simulated or natural and should, in any event, (i) be organoleptically compatible with the isobutyl substituted heterocyclic compounds and/or mixtures of same of our invention by not covering or spoiling the organoleptic properties (aroma and/or taste) thereof; (ii) be non-reactive with the isobutyl substituted heterocyclic compounds and/or mixtures of same of our invention, and (iii) be capable of providing an environment in which the isobutyl substituted heterocyclic compounds and/or mixtures of same can be dispersed or admixed to provide a homogeneous medium. In addition, selection of one or more flavoring adjuvants, as well as the quantities thereof, will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of isobutyl substituted heterocyclic compounds and/or mixtures of same employed in a particular instance can vary over a relatively wide range, depending upon the desired organoleptic effects to be achieved. Thus, correspondingly, greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected be effective, i.e., sufficient to alter, modify or enhance the organoleptic characteristics of the parent composition whether foodstuff per se, chewing gum per se, medicinal product per se, toothpaste per se, or flavoring composition.

The use of insufficient quantities of isobutyl substituted heterocyclic compounds and/or mixtures of same will, of course, substantially vitiate any possibility of obtaining the desired results while excess quantities prove needlessly costly and in extreme cases, any disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of isobutyl substituted heterocyclic compounds and/or mixtures of same ranging from a small but effective amount, e.g., 5.0 parts per million up to about 100 parts per million based on total composition are suitable. Concentrations in excess of the maximum quantity stated are not normally recommended since they fail to prove commensurate enhancement of organoleptic properties. In those instances, wherein the isobutyl substituted heterocyclic compounds and/or mixtures of same are added to the foodstuff as integral components of a flavoring composition, it is, of course, essential that the total quantity of flavoring composition employed be sufficient to yield an effective isobutyl substituted heterocyclic compounds and/or mixtures of same concentration in the foodstuff products.

Food flavoring compositions prepared in accordance with the present invention preferably contain the isobutyl substituted heterocyclic compounds and/or mixtures of same in concentrations ranging from about 0.1% up to about 15% by weight based on the total weight of the said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the isobutyl substituted heterocyclic compounds and/or mixtures of same with, for example, gum arabic, gum tragacanth, carageenan and the like, and thereafter spray-drying the resultant mixture whereby to obtain the particular solid product. Pre-prepared flavor mixes in powder form, e.g., a fruit-flavored powder mix, are obtained by mixing the dried solid components, e.g., starch, sugar and the like, and isobutyl substituted heterocyclic compounds and/or mixtures of same in a dry blender until the requisite degree of uniformity is achieved.

It is presently preferred to combine with the isobutyl substituted heterocyclic compounds and/or mixtures of same of our invention the following adjuvants:

p-Hydroxybenzyl acetone;
Geraniol;
Cassia Oil;
Acetaldehyde;
Maltol;
Ethyl methyl phenyl glycidate;
Benzyl acetate;
Dimethyl sulfide;
Eugenol;
Vanillin;
Caryophyllene;
Methyl cinnamate;
Guaiacol;
Ethyl pelargonate;
Cinnamaldehyde;
Methyl anthranilate;
5-Methyl furfural;
Isoamyl acetate;
Isobutyl acetate;
Cuminaldehyde;
Alpha ionone;
Cinnamyl formate;
Ethyl butyrate;
Acetic acid;
Gamma-undecalactone;
Naphthyl ethyl ether;
Diacetyl;
Furfural;
Ethyl acetate;
Anethole;
2,3-Dimethyl pyrazine;
2-Ethyl-3-methyl pyrazine;
3-Phenyl-4-pentenal
2-Phenyl-2-hexenal;
2-Phenyl-2-pentenal;
3-Phenyl-4-pentenal diethyl acetal;
Damascone (1-crotonyl-2,2,6-trimethylcyclohexen-1-one)
Damascenone (1-crotonyl-2,2,6-trimethylcyclohexa-1,5-diene)
Beta-cyclohomocitral (2,2,6-trimethyl-cyclohex-1-ene carboxaldehyde)
Isoamyl butyrate;
Cis-3-hexenol-1;
2-Methyl-2-pentenoic acid;
Elemecine (4-allyl-1,2,6-trimethoxy benzene);
Isoelemecine (4-propenyl-1,2,6-trimethoxy benzene); and
2-(4-Hydroxy-4-methylpentyl) norborandiene prepared according to U.S. Application for Letters Pat. No. 461,703, filed on Apr. 17, 1974
2-Methoxy-3-isobutylpyrazine;
2,4,5-Trimethylthiazole;
2-Methyl-5-methoxy-4-isobutylthiazole;
2,4-Dimethyl-5-acetylthiazole;
2,4-Dimethyl-5-ethylthiazole;
2(2-Methylthioethyl)-$\Delta^3$-thiazoline;
2-Secondary butyl-$\Delta^3$thiazoline;
2-n-Butyl-$\Delta^3$-thiazoline;
2-Isobutyl-$\Delta^3$-thiazoline;
2-Pentyl-$\Delta^3$-thiazoline;
2-Hexyl-$\Delta^3$-thiazoline;
2-Benzyl-$\Delta^3$-thiazoline;

2-Secondary butyl thiazole;
2-n-Butyl thiazole;
2-Phenyl-4-pentenal;
Isovaleraldehyde;
2-Phenyl-2-butenal;
4-Methyl-2-phenyl-2-pentenal;
5-Methyl-2-phenyl-2-hexenal;

An additional aspect of our invention provides an organoleptically improved smoking tobacco product and additives therefor, as well as methods of making the same which overcome specific problems heretofore encountered in which specific desired chocolate-like, cocoa-like and sweet, creamy aroma and flavor prior to smoking and a chocolate-like aroma and more tobacco-like nuances on smoking in the main stream and side stream, are created or enhanced or modified or augmented and may be readily controlled and maintained at the desired level regardless of variations in the tobacco components of the blend.

This invention further provides improved tobacco additives and methods whereby desirable chocolate-like, cocoa-like and sweet, creamy aroma and flavor prior to smoking and a chocolate-like aroma and more tobacco-like nuances on smoking in the main stream and side stream may be imparted to smoking tobacco products and may be readily varied and controlled to produce the desired uniform flavoring characteristics.

In carrying out this aspect of our invention, we add to smoking tobacco materials or a suitable substitute therefor (e.g., dried lettuce leaves) an aroma and flavor additive containing as an active ingredient the isobutyl substituted heterocyclic compounds and/or mixtures of same of our invention.

In addition to the isobutyl substituted heterocyclic compounds and/or mixtures of same of our invention, other flavoring and aroma additives may be added to the smoking tobacco material or substitute therefor either separately or in mixture with the isobutyl substituted heterocyclic compounds and/or mixtures of same as follows:

I. Synthetic Materials:
  Beta-ethyl-cinnamaldehyde;
  Eugenol;
  Dipentene;
  Damascenone;
  Maltol;
  Ethyl maltol;
  Delta undecalactone;
  Delta decalactone;
  Benzaldehyde;
  Amyl acetate;
  Ethyl butyrate;
  Ethyl valerate;
  Ethyl acetate;
  2-Hexenol-1;
  2-Methyl-5-isopropyl-1,3-nonadiene-8-one;
  2,6-Dimethyl-2,6-undecadiene-10-one;
  2-Methyl-5-isopropyl acetophenone;
  2-Hydroxy-2,5,5-8a-tetramethyl-1-(2-hydroxyethyl)-decahydronaphthalene;
  Dodecahydro-3a,6,6-9a-tetramethyl naphtho-(2,1b)-furan;
  4-Hydroxy hexanoic acid, gamma lactone; and
  Polyisoprenoid hydrocarbons defined in Example V of U.S. Pat. No. 3,589,372 issued on June 29, 1971.

II. Natural Oils
  Celery seed oil;
  Coffee extract;
  Bergamot Oil;
  Cocoa extract;
  Nutmeg oil; and
  Origanum oil.

An aroma and flavoring concentrate containing isobutyl substituted heterocyclic compounds and/or mixtures of same and, if desired, one or more of the above-indicated additional flavoring additives may be added to the smoking tobacco material, to the filter or to the leaf or paper wrapper. The smoking tobacco may be shredded, cured, cased and blended tobacco material or reconstituted tobacco material or tobacco substitutes (e.g., lettuce leaves) or mixtures thereof. The proportions of flavoring additives may be varied in accordance with taste, but insofar as the enhancement or the imparting of chocolate-like, cocoa-like, nutty, green, burnt roasted and sweet, creamy notes, we have found that satisfactory results are obtained if the proportion by weight of the sum total of isobutyl substituted heterocyclic compounds and/or mixtures of same to smoking tobacco material is between 250 ppm and 1,500 ppm (0.025%–0.15%) of the active ingredients to the smoking tobacco material. We have further found that satisfactory results are obtained if the proportion by weight of the sum total of isobutyl substituted heterocyclic compounds and/or mixtures of same used to flavoring material is between 2,500 and 15,000 ppm (0.25%–1.5%).

Any convenient method for incorporating the isobutyl substituted heterocyclic compounds and/or mixtures of same into the tobacco product may be employed. Thus, isobutyl substituted heterocyclic compounds and/or mixtures of same taken alone or along with other flavoring additives may be dissolved in a suitable solvent such as ethanol, diethyl ether and/or volatile organic solvents, and the resulting solution may either be spread on the cured, cased and blended tobacco material or the tobacco material may be dipped into such solution. Under certain circumstances, a solution of isobutyl substituted heterocyclic compounds and/or mixtures of same taken alone or taken further together with other flavoring additives as set forth above, may be applied by means of a suitable applicator such as a brush or roller on the paper or leaf wrapper for the smoking product, or it may be applied to the filter by either spraying, or dipping, or coating.

Furthermore, it will be apparent that only a portion of the tobacco or substitute therefor need be treated and the thus-treated tobacco may be blended with other tobaccos before the ultimate tobacco product is formed. In such cases, the tobacco treated may have the isobutyl substituted heterocyclic compounds and/or mixtures of same in excess of the amounts or concentrations above indicated so that when blended with other tobaccos, the final product will have the percentage within the indicated range.

In accordance with one specific example of our invention, an aged, cured and shredded domestic burley tobacco is spread with a 20% ethyl alcohol solution of 2,4,6-triisobutyl-1,3,5-trioxane having the structure:

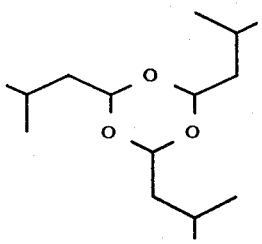

in an amount to provide a tobacco composition containing 800 ppm by weight of 2,4,6-triisobutyl-1,3,5-trioxane on a dry basis. Thereafter, the alcohol is removed by evaporation and the tobacco is manufactured into cigarettes by the usual techniques. The cigarette when treated as indicated has a desired and pleasing aroma which is detectable in the main and side streams when the cigarette is smoked. This aroma is described as being more tobacco-like and having chocolate-like and cocoa-like notes.

While our invention is particularly useful in the manufacture of smoking tobacco, such as cigarette tobacco, cigar tobacco and pipe tobacco, other tobacco products formed from sheeted tobacco dust or fines may also be used. Likewise, the isobutyl substituted heterocyclic compounds and/or mixtures of same of our invention can be incorporated with materials such as filter tip materials, seam paste, packaging materials and the like which are used along with tobacco to form a product adapted for smoking. Furthermore, the isobutyl substituted heterocyclic compounds and/or mixtures of same can be added to certain tobacco substitutes of natural or synthetic origin (e.g., dried lettuce leaves) and, accordingly, by the term "tobacco" as used throughout this specification is meant any composition intended for human consumption by smoking or otherwise, whether composed of tobacco plant parts or substituted materials or both.

It will thus be apparent that the isobutyl substituted heterocyclic compounds and/or mixtures of same of our invention can be utilized to alter, modify or enhance sensory properties, particularly organoleptic properties, such as flavor(s) and/or aroma(s) of a wide variety of consumable materials including foodstuffs and tobaccos.

The following examples illustrate processes for specifically producing isobutyl substituted heterocyclic compounds and/or mixtures of same of our invention and also serve to illustrate the organoleptic qualities of isobutyl substituted heterocyclic compounds and/or mixtures of same and, in addition, the uses of isobutyl substituted heterocyclic compounds and/or mixtures of same for their organoleptic properties.

EXAMPLE I

PREPARATION OF 2,4,6-TRIISOBUTYL-1,3,5-TRIOXANE

Reaction:

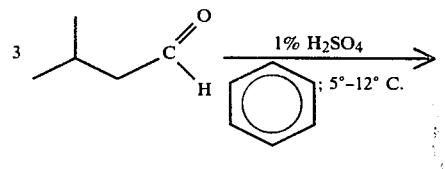

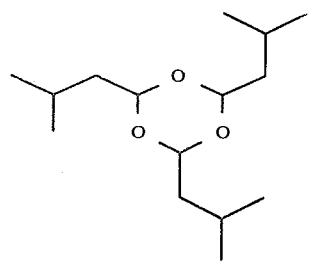

Into a one liter, three-necked reaction flask equipped with mechanical stirrer, condenser, immersion thermometer, "Y" adapter and cold bath is placed 200 ml of isovaleraldehyde and 100 ml of benzene. The resulting mixture is cooled to about 5° C. using a ice-water bath. 2 Grams of concentrated sulfuric acid is then added dropwise to the reaction mixture while it is being agitated using the mechanical stirrer. The reaction mass heats up to a temperature of about 12° C.

The reaction mass is then stirred for a period of 19 hours at a temperature of about 22° C. The resulting reaction product is made basic by washing with five 20 ml portions of 5% aqueous sodium hydroxide. The resulting product is then washed to neutral with two 50 ml portions of water. The resulting product is then distilled at 95° C. and 1 mm Hg yielding 2,4,6-triisobutyl-1,3,5-trioxane.

FIG. 1 sets forth the NMR spectrum for the resulting product, 2,4,6-triisobutyl-1,3,5-trioxane.

Figure 2:
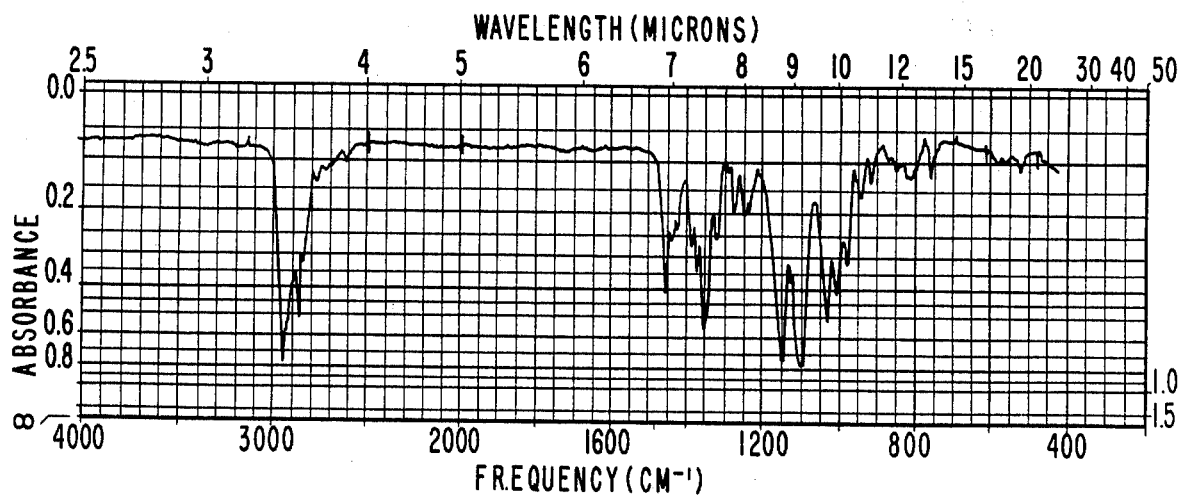
FIG. 2 represents the infrared spectrum for 2,4,6-triisobutyl-1,3,5-trioxane produced according to Example I.

FIG. 2 sets forth the infrared spectrum for the resulting product, 2,4,6-triisobutyl-1,3,5-trioxane.

Figure 3:
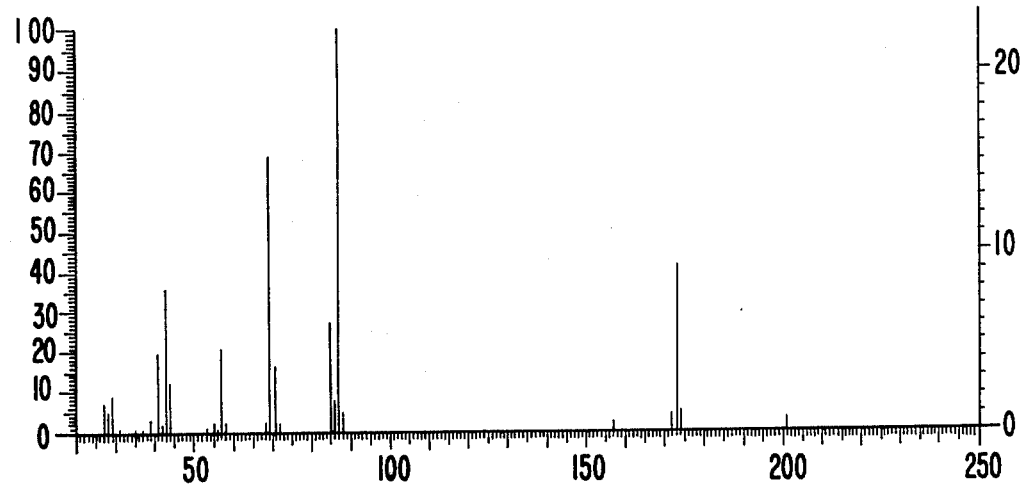
FIG. 3 represents the mass spectrum for 2,4,6-triisobutyl-1,3,5-trioxane produced according to Example I.

FIG. 3 sets forth the mass spectrum for the resulting product, 2,4,6-triisobutyl-1,3,5-trioxane.

The resulting material, when added to tobacco, gives rise to a chocolate-like, cocoa-like and sweet, creamy flavor and aroma prior to smoking; and a chocolate-like aroma nuance with more tobacco-like nuances on smoking in the main stream and the side stream. In foodstuffs the resultant material gives rise to sweet, dairy-like, creamy, vanilla, berry-like, milk chocolate-like and cocoa butter-like aromas and sweet, dairy-like, creamy, vanilla, berry-like, milk chocolate and cocoa butter-like flavor characteristics.

The resulting 2,4,6-triisobutyl-1,3,5-trioxane is then compared with isovaleraldehyde at about the same intensity insofar as their taste characteristics are concerned:

At the rate of 10 ppm for 2,4,6-triisobutyl-1,3,5-trioxane;

At the rate of 0.1 ppm for isovaleraldehyde. The 2,4,6-triisobutyl-1,3,5-trioxane has a cocoa/floral aroma and taste as found in dark chocolate. The isovaleraldehyde is substantially weaker in aroma notes at about the same flavor strength for both chemicals. Its aroma and taste characteristics are more cocoa powder-like. Therefore, both chemicals are completely different in their aroma and taste characteristics.

EXAMPLE II

PREPARATION OF ISOBUTYL SUBSTITUTED HETEROCYCLIC COMPOUNDS

Reaction:

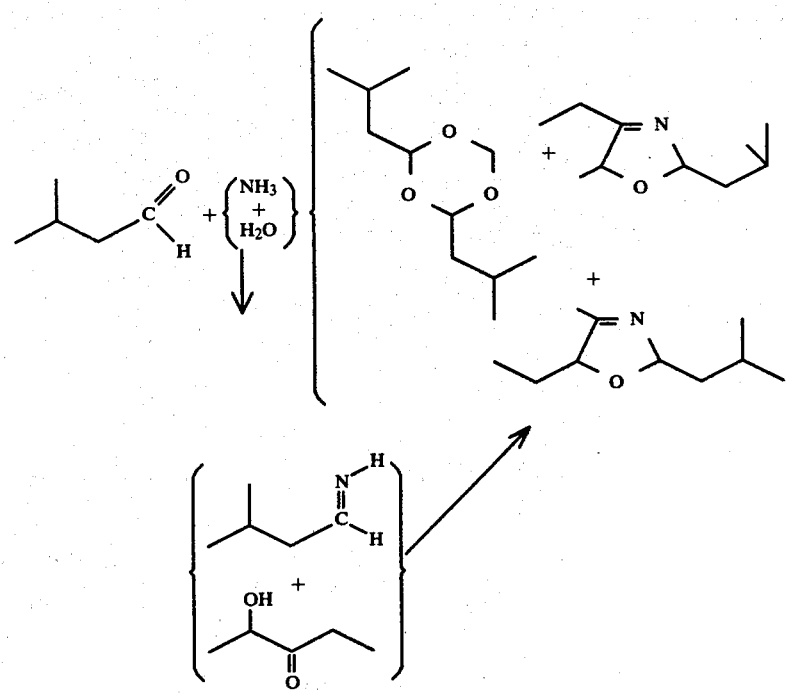

Into a 500 ml reaction flask equipped with mechanical stirrer, 250 ml addition funnel, thermometer, "Y" adapter, Freidrich condenser and isopropanol/dry ice bath is placed 86.2 ml of aqueous ammonia (0.5 moles). The aqueous ammonia is cooled to 3° C. Dropwise, with stirring, is added 43 grams of isovaleraldehyde. On completion of the addition of the isovaleraldehyde, the resulting imine forms a solid mass in the aqueous medium which is dispersed at a temperature of about 35° C. The addition time of the isovaleraldehyde is 1.5 hours.

The resulting reaction mass is stirred for an additional 1.5 hours before the dropwise addition of 51.9 grams of 2(3)-hydroxy-3(2)-pentanone. The reaction between the 2(3)-hydroxy-3(2)-pentanone and the imine is carried out for a period of two hours. The resulting reaction mass now exists in two phases. The aqueous phase is extracted with three 100 ml portions of diethyl ether and combined with the organic phase. The combined organic phases are then washed with three 100 ml portions of saturated sodium chloride solution.

The resulting product is fractionally distilled at 110° C. and 10 mm Hg to yield a large number of products, one of which is 2,4,6-triisobutyl-1,3,5-trioxane.

The NMR spectrum for 2,4,6-triisobutyl-1,3,5-trioxane is set forth in FIG. 1. The IR spectrum for 2,4,6-triisobutyl-1,3,5-trioxane is set forth in FIG. 2. The mass spectrum for 2,4,6-triisobutyl-1,3,5-trioxane is set forth in FIG. 3.

The mass spectrum is as follows:

| m/e | Relative intensity |
|-----|--------------------|
| 41  | 19                 |
| 43  | 35                 |
| 44  | 12                 |
| 45  | 16                 |
| 57  | 20                 |
| 69  | 69                 |
| 71  | 16                 |
| 85  | 27                 |
| 87  | 100                |

-continued

| m/e | Relative intensity |
|-----|--------------------|
| 173 | 41                 |
| 258 | 0                  |

Figure 4:
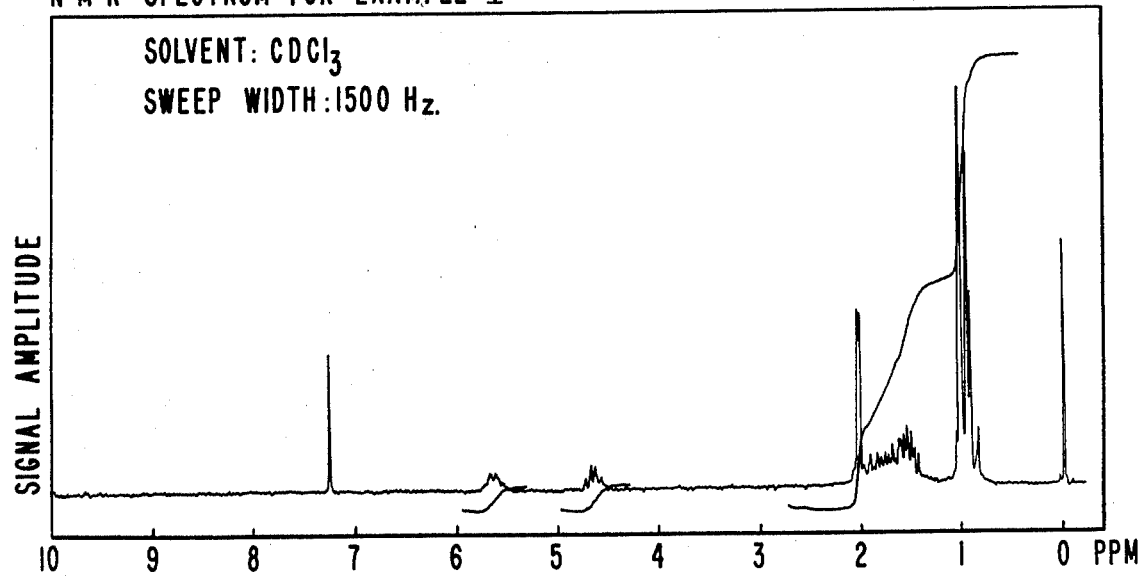
FIG. 4 represents the NMR spectrum for 5-ethyl-4-methyl-2-isobutyl-3-oxazoline (fraction 2-5, peak 2) produced according to Example II.
Figure 5:
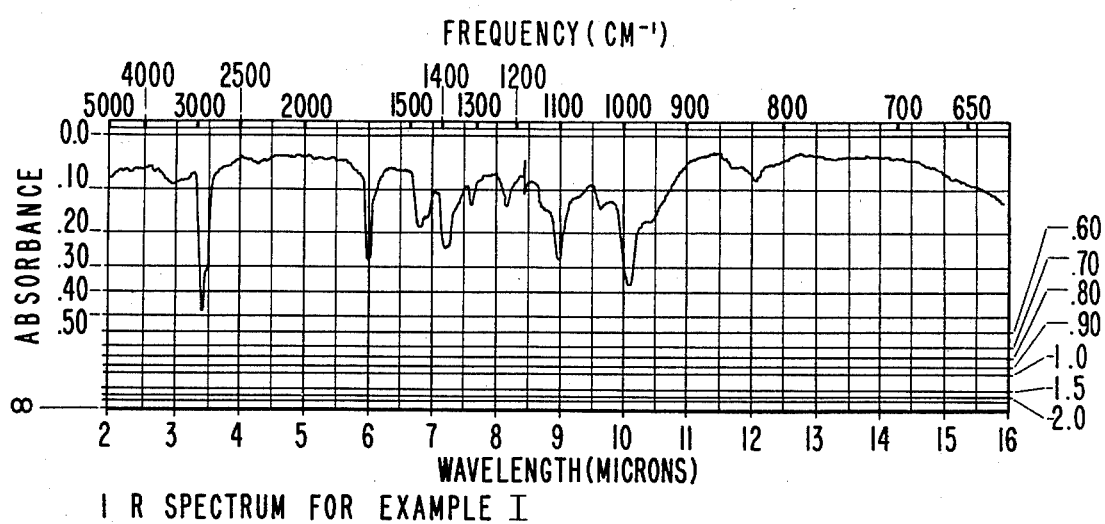
FIG. 5 represents the infrared spectrum for 5-ethyl-4-methyl-2-isobutyl-3-oxazoline (fraction 2-5, peak 2) produced according to Example II.
Figure 6:
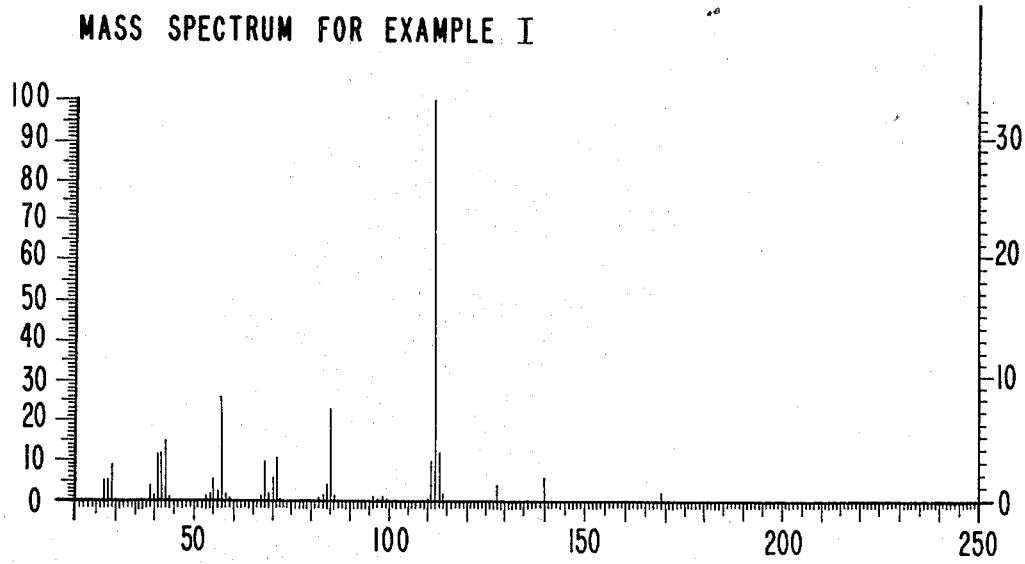
FIG. 6 represents the mass spectrum for 5-ethyl-4-methyl-2-isobutyl-3-oxazoline produced according to Example II.

FIG. 4 represents the NMR spectrum for 5-ethyl-4-methyl-2-isobutyl-3-oxazoline resulting from distillation of fraction 2-5 followed by GLC preparative chromatography on Carbowax 20M. FIG. 5 represents the infrared spectrum for 5-ethyl-4-methyl-2-isobutyl-3-oxazoline. FIG. 6 represents the mass spectrum for 5-ethyl-4-methyl-2-isobutyl-3-oxazoline.

Figure 7:
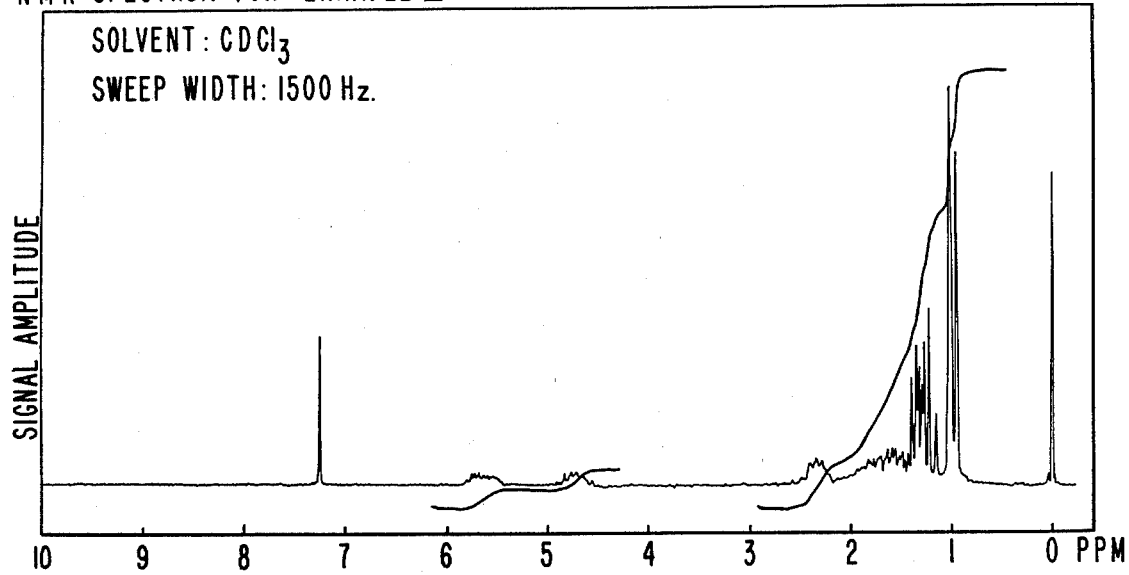
FIG. 7 represents the NMR spectrum for 4-ethyl-5-methyl-2-isobutyl-3-oxazoline (fraction 2-5, peak 1) produced according to Example II.
Figure 8:
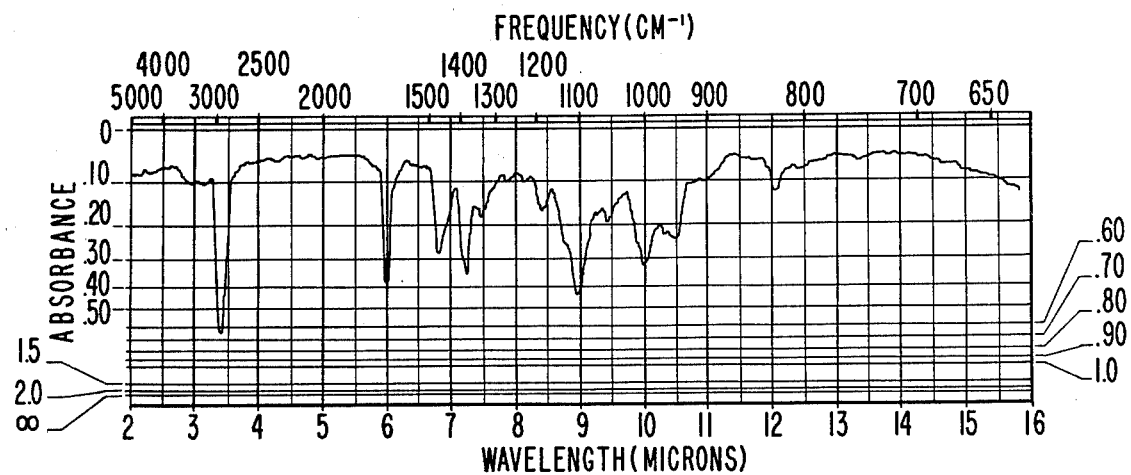
FIG. 8 represents the infrared spectrum for 4-ethyl-5-methyl-2-isobutyl-3-oxazoline (fraction 2-5, peak 1) produced according to Example II.
Figure 9:
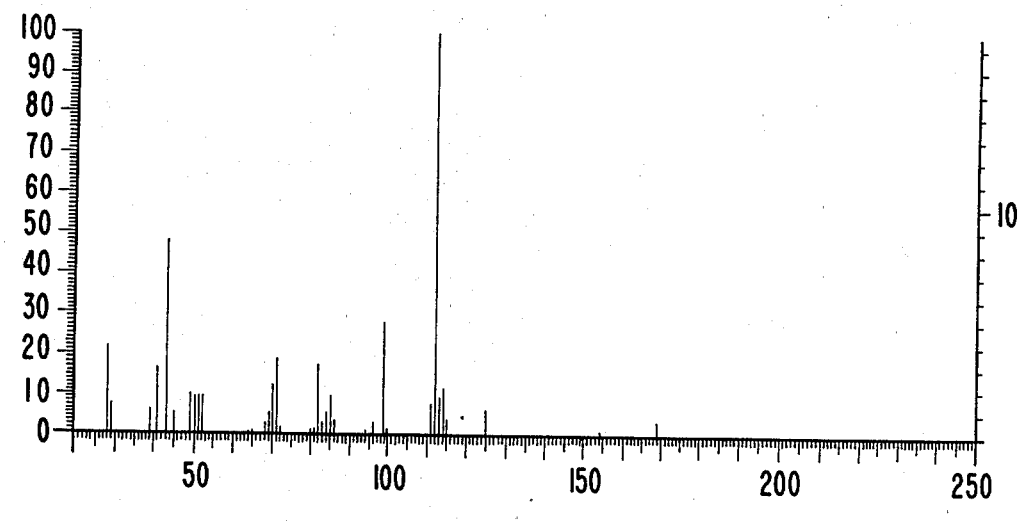
FIG. 9 represents the mass spectrum for 4-ethyl-5-methyl-2-isobutyl-3-oxazoline produced according to Example II.

FIG. 7 represents the NMR spectrum for 4-ethyl-5-methyl-2-isobutyl-3-oxazoline which is peak 1 separated from fraction 2-5 by preparative GLC using a Carbowax 20M column. FIG. 8 represents the infrared spectrum for 4-ethyl-5-methyl-2-isobutyl-3-oxazoline. FIG. 9 represents the mass spectrum for 4-ethyl-5-methyl-2-isobutyl-3-oxazoline.

EXAMPLE III

TOBACCO FORMULATION

A tobacco mixture is produced by admixing the following ingredients:

| Ingredient       | Parts by Weight |
|------------------|-----------------|
| Bright           | 40.1            |
| Burley           | 24.9            |
| Maryland         | 1.1             |
| Turkish          | 11.6            |
| Stem (flue-cured)| 14.2            |
| Glycerine        | 2.8             |
| Water            | 5.3             |

Cigarettes are prepared from this tobacco. The following flavor formulation is prepared:

| Ingredient | Parts by Weight |
| --- | --- |
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above-stated tobacco flavor formulation is applied at the rate of 0.1% to all of the cigarettes produced using the above tobacco formulation. Half of the cigarettes are then treated with 500 or 1,000 ppm of 2,4,6-triisobutyl-1,3,5-trioxane produced according to the process of Example I. The control cigarettes not containing the 2,4,6-triisobutyl-1,3,5-trioxane and the experimental cigarettes which contain the 2,4,6-triisobutyl-1,3,5-trioxane produced according to the process of Example I are evaluated by paired comparison, and the results are as follows:

The experimental cigarettes are found, on smoking, to have very pleasant chocolate-like aroma notes and to be more tobacco-like.

The tobacco of the experimental cigarettes, prior to smoking, has chocolate-like, cocoa-like and sweet-creamy notes.

All cigarettes are evaluated for smoke flavor with a 20 mm cellulose acetate filter.

EXAMPLE IV

RASPBERRY FLAVOR FORMULATION

The following basic raspberry flavor formulation is produced:

| Ingredient | Parts by Weight |
| --- | --- |
| Vanillin | 2.0 |
| Maltol | 5.0 |
| Parahydroxybenzylacetone | 5.0 |
| Alpha-ionone (10% in propylene glycol) | 2.0 |
| Ethyl butyrate | 6.0 |
| Ethyl acetate | 16.0 |
| Dimethyl sulfide | 1.0 |
| Isobutyl acetate | 13.0 |
| Acetic acid | 10.0 |
| Acetaldehyde | 10.0 |
| Propylene glycol | 930.0 |

2,4,6-Triisobutyl-1,3,5-trioxane is added to half of the above formulation at the rate of 5.0%. The formulation with the 2,4,6-triisobutyl-1,3,5-trioxane is compared with the formulation without the 2,4,6-triisobutyl-1,3,5-trioxane at the rate of 0.01% (100 ppm) in water and evaluated by a bench panel.

The flavor containing the 2,4,6-triisobutyl-1,3,5-trioxane is found to have substantially sweeter aroma notes and a sweet raspberry, raspberry kernel-like and sweet aftertaste and mouthfeel missing in the basic raspberry formulation. It is the unanimous opinion of the bench panel that the chemical, 2,4,6-triisobutyl-1,3,5-trioxane rounds the flavor out and contributes to a very natural fresh aroma and taste as found in full ripe raspberries.

EXAMPLE V

A. POWDER FLAVOR COMPOSITION

70 Grams of the flavor composition of Example IV is emulsified in a solution containing 310 gm gum acacia and 620 gm water. The emulsion is spray-dried with a Bowen Lab Model Drier utilizing 260 c.f.m. of air with an inlet temperature of 500° F., an outlet temperature of 200° F., and a wheel speed of 50,000 r.p.m.

B. SUSTAINED RELEASE FLAVOR

The following mixture is prepared:

| Ingredient | Parts by Weight |
| --- | --- |
| Liquid Raspberry Flavor Composition of Example IV | 20 |
| Propylene glycol | 9 |
| Cab-O-Sil ® M-5 (Brand of Silica produced by the Cabot Corporation of 125 High Street, Boston, Mass. 02110; Physical Properties: Surface Area: 200 m²/gm Nominal particle size: 0.012 microns Density: 2.3 lbs/cu.ft.) | 5.00 |

The Cab-O-Sil is dispersed in the liquid raspberry flavor composition of Example IV with vigorous stirring, thereby resulting in a viscous liquid. 71 Parts by weight of the powder flavor composition of Part A, supra, is then blended into the said viscous liquid, with stirring at 25° C. for a period of 30 minutes resulting in a dry, free flowing sustained release flavor powder.

EXAMPLE VI

SOLID FLAVOR

10 Parts by weight of 50 Bloom pigskin gelatin is added to 90 parts by weight of water at a temperature of 150° F. The mixture is agitated until the gelatin is completely dissolved and the solution is cooled to 120° F. 20 Parts by weight of the liquid flavor composition of Example IV is added to the solution which is then homogenized to form an emulsion having particle size typically in the range of 2–5 microns. This material is kept at 120° F. under which conditions the gelatin will not gel.

Coascervation is induced by adding, slowly and uniformly, 40 parts by weight of a 20% aqueous solution of sodium sulphate. During coascervation, the gelatin molecules are deposited uniformly about each oil droplet as a nucleus.

Gelation is effected by pouring the heated coascervate mixture into 1,000 parts by weight of 7% aqueous solution of sodium sulphate at 65° F. The resulting jelled coascervate may be filtered and washed with water at temperatures below the melting point of gelatin, to remove the salt.

Hardening of the filtrate, in this example, is effected by washing with 200 parts by weight of 37% solution of formaldehyde in water. The cake is then washed to remove residual formaldehyde.

EXAMPLE VII

CHEWING GUM

100 Parts by weight of chicle are mixed with 4 parts by weight of the flavor prepared in accordance with Example V. 300 Parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long-lasting raspberry flavor.

EXAMPLE VIII

CHEWING GUM

100 Parts by weight of chicle are mixed with 18 parts by weight of the flavor prepared in accordance with Example VI. 300 Parts of sucrose and 100 parts of corn syrup are then added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long-lasting raspberry flavor.

EXAMPLE IX

TOOTHPASTE FORMULATION

The following separate groups of ingredients are prepared:

| Parts by Weight | Ingredient |
|---|---|
| Group "A" | |
| 30.200 | Glycerin |
| 15.325 | Distilled Water |
| .100 | Sodium Benzoate |
| .125 | Saccharin Sodium |
| .400 | Stannous Flouride |
| Group "B" | |
| 12.500 | Calcium Carbonate |
| 37.200 | Dicalcium Phosphate (Dihydrate) |
| Group "C" | |
| 2.000 | Sodium K-Lauroyl Sarcosinate (foaming agent) |
| Group "D" | |
| 1.200 | Flavor Material of Example V |
| 100.00 (Total) | |

PROCEDURE:
1. The ingredients in Group "A" are stirred and heated in a steam jacketed kettle to 160° F.
2. Stirring is continued for an additional three to five minutes to form a homogenous gel.
3. The powders of Group "B" are added to the gel, while mixing until a homogenous paste is formed.
4. With stirring, the flavor of "D" is added and lastly the sodium n-lauryl sarcosinate.
5. The resultant slurry is then blended for n-lauroyl hour. The completed paste is then transferred to a three roller mill and then homogenized, and finally tubed.

The resulting toothpaste when used in a normal toothbrushing procedure yields a pleasant raspberry flavor, of constant strong intensity throughout said procedure (1-1.5 minutes).

EXAMPLE X

CHEWABLE VITAMIN TABLETS

The flavor material produced according to the process of Example VI is added to a Chewable Vitamin Tablet Formulation at a rate of 10 gm/Kg which Chewable Vitamin Tablet Formulation is prepared as follows:

In a Hobart Mixer, the following materials are blended to homogeneity:

| | Gms/1000 tablets |
|---|---|
| Vitamin C (ascorbic acid) as ascorbic acid-sodium ascorbate mixture 1:1 | 70.0 |
| Vitamin $B_1$ (thiamine mononitrate) | |
| as Rocoat ® thiamine mononitrate 33 ⅓% (Hoffman La Roche) | 4.0 |
| Vitamin $B_2$ (riboflavin) as Rocoat ® riboflavin 33 ⅓% | 5.0 |
| Vitamin $B_6$ (pyridoxine hydrochloride) as Rocoat ® pyridoxine hydrochloride 33 ⅓% | 4.0 |
| Niacinamide as Rocoat ® niacinamide 33 ⅓% | 33.0 |
| Calcium pantothenate | 11.5 |
| Vitamin $B_{12}$ (cyanocobalamin) as Merck 0.1% in gelatin | 3.5 |
| Vitamin E (dl-alpha tocopheryl acetate) as dry Vitamin E acetate 33 ⅓% Roche | 6.6 |
| d-Biotin | 0.044 |
| Certified lake color | 5.0 |
| Flavor of Example VI | (as indicated above) |
| Sweetener - sodium saccharin | 1.0 |
| Magnesium stearate lubricant | 10.0 |
| Mannitol q.s. to make | 500.0 |

Preliminary tablets are prepared by slugging with flat-faced punches and grinding the slugs to 14 mesh. 13.5 g dry Vitamin A Acetate and 0.6 g Vitamin D are then added as beadlets. The entire blend is then compressed using concave punches at 0.5 g each.

Chewing of the resultant tablets yields a pleasant, long-lasting, consistently strong raspberry flavor for a period of 12 minutes.

EXAMPLE XI

CHEWING TOBACCO

Onto 100 pounds of tobacco for chewing (85% Wisconsin leaf and 15% Pennsylvania leaf) the following casing is sprayed at a rate of 30%:

| Ingredients | Parts by Weight |
|---|---|
| Corn Syrup | 60 |
| Licorice | 10 |
| Glycerine | 20 |
| Fig Juice | 4.6 |
| Prune Juice | 5 |
| Flavor Material of Example V | 0.4 |

The resultant product is redried to a moisture content of 20%. On chewing, this tobacco has an excellent substantially consistent, long-lasting raspberry (20 minutes) nuance in conjunction with the main fruity tobacco note.

EXAMPLE XII

COCOA FLAVOR

The following basic cocoa formulation is prepared by admixing the following ingredients:

| Ingredients | Parts by Weight |
|---|---|
| Vanillin | 6.5 |
| Amylphenyl acetate | 3.5 |
| Benzyl butyrate | 0.5 |
| Veratraldehyde | 0.5 |
| 5-Methyl-2-phenyl-2-hexenal | 3.0 |
| Isovaleraldehyde | 4.0 |
| Isobutyraldehyde | 1.0 |
| Benzaldehyde | 0.2 |
| 5-Methyl furfural | 0.8 |

-continued

| Ingredients | Parts by Weight |
| --- | --- |
| Propylene glycol | 80.0 |

The foregoing flavor formulation is divided into two portions. To a first portion, 10% by weight of 2,4,6-triisobutyl-1,3,5-trioxane prepared according to Example I, is added. Nothing is added to the second portion. Both flavors are compared at the rate of 20 ppm in water. The flavor containing the 2,4,6-triisobutyl-1,3,5-trioxane has a characteristic cocoa-butter note, both in aroma and in taste. This characteristic cocoa-butter note is missing in the basic flavor formulation without said 2,4,6-triisobutyl-1,3,5-trioxane. Therefore, a bench panel, composed of three individuals, prefers the formulation which contains the 2,4,6-triisobutyl-1,3,5-trioxane.

EXAMPLE XIII

CHOCOLATE FORMULATION

The following basic chocolate formulation is prepared:

| Ingredients | Parts by Weight |
| --- | --- |
| Maltol | 0.30 |
| Isobutyraldehyde | 1.50 |
| Isovaleraldehyde | 4.20 |
| Propylene glycol | 3.00 |
| Dimethyl sulfide | 0.05 |
| Isobutyl acetate | 0.10 |
| Isoamyl acetate | 0.20 |
| Phenylethyl acetate | 0.05 |
| Diacetyl (10% in food grade ethyl alcohol) | 0.05 |
| Furfural (10% in food grade ethyl alcohol) | 0.10 |
| Benzaldehyde | 0.10 |
| Isoamyl alcohol | 0.05 |
| Phenylethyl alcohol | 0.30 |

In addition, a chocolate-like flavor composition is prepared with the following ingredients:

| Ingredients | Parts by Weight |
| --- | --- |
| Trimethylthiazole (10% in food grade ethyl alcohol) | 2.0 |
| Tetramethylpyrazine | 4.0 |
| 2,4,6-Triisobutyl-1,3,5-trioxane (prepared according to Example I) | 2.0 |
| Food grade ethanol | 2.0 |

The basic chocolate formulation is divided into two portions. To a first portion, 10% by weight of the "chocolate-like flavor composition" containing the 2,4,6-triisobutyl-1,3,5-trioxane, is added. To the second portion, nothing is added. Both flavors with and without the additional material are compared at the rate of 20 ppm in water. The flavor with the additional "chocolate-like flavor composition" has a full dark chocolate aroma and taste with a sweet, milk chocolate undertone. These notes are missing in the basic formulation without the addition of the "chocolate-like flavor composition". The added "chocolate-like flavor composition" causes the "basic chocolate formulation" to be preferred by a bench panel composed of three individuals.

EXAMPLE XIV

COCOA FLAVOR

The following basic cocoa formulation is prepared:

| Ingredients | Parts by Weight |
| --- | --- |
| Vanillin | 6.5 |
| Amylphenyl acetate | 3.5 |
| Benzyl butyrate | 0.5 |
| Veratraldehyde | 0.5 |
| 5-Methyl-2-phenyl-2-hexenal | 3.0 |
| Isovaleraldehyde | 4.0 |
| Isobutyraldehyde | 1.0 |
| Benzaldehyde | 0.2 |
| 5-Methyl furfural | 0.8 |
| Propylene glycol | 80.0 |

The above basic cocoa formulation is divided into two portions. To a first portion, 7.5% by weight of 4-ethyl-2-isobutyl-5-methyl-3-oxazoline, prepared according to Example II, is added. To the second portion, nothing is added. Both flavor formulations with and without the additional 4-ethyl-2-isobutyl-5-methyl-3-oxazoline, are compared at the rate of 20 ppm in water. The flavor containing the 4-ethyl-2-isobutyl-5-methyl-3-oxazoline has a deeper, cocoa character, more mouthfeel and a "light hydrolyzed vegetable protein-like" note. It is therefore preferred by a bench panel composed of three individuals.

EXAMPLE XV

TOBACCO FORMULATION

A tobacco mixture is produced by admixing the following ingredients:

| Ingredients | Parts by Weight |
| --- | --- |
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco.
The following flavor formulation is prepared:

| Ingredients | Parts by Weight |
| --- | --- |
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above-stated tobacco flavor formulation is applied at the rate of 0.1% to all of the cigarettes produced using the above tobacco formulation. Half of the cigarettes are then treated with 500 or 1,000 ppm of 4-ethyl-2-isobutyl-5-methyl-3-oxazoline produced according to the process of Example II. The control cigarettes not containing the 4-ethyl-2-isobutyl-5-methyl-3-oxazoline and the experimental cigarettes which contain the said oxazoline produced according to the process of Example II are evaluated by paired comparison, and the results are as follows:

The experimental cigarettes are found, on smoking, to have very pleasant chocolate-like, nutty, green and burnt roasted-like aroma notes and to be more tobacco-like.

The tobacco of the experimental cigarettes, prior to smoking, has chocolate-like, nutty, green notes.

All cigarettes are evaluated for smoke flavor with a 20 mm cellulose acetate filter.

EXAMPLE XVI

USE OF 5-ETHYL-4-METHYL-2-ISOBUTYL-3-OXAZOLINE TO ENHANCE THE VEGETABLE FLAVOR OF VEGETARIAN VEGETABLE SOUP

5-Ethyl-4-methyl-2-isobutyl-3-oxazoline produced according to Example II is added at the rate of 2 ppm to condensed vegetarian vegetable soup (Shop-Rite ® brand). One liter of water is added to one liter of soup and thoroughly admixed. The resulting mixture is then simmered (temperature=200° F.) for a period of ten minutes. The resulting soup is compared by a bench panel with a soup which has no 5-ethyl-4-methyl-2-isobutyl-3-oxazoline added thereto. The soup having the 5-ethyl-4-methyl-2-isobutyl-3-oxazoline prepared according to Example II is unanimously preferred as having a more vegetable-like taste with excellent cooked green pepper, spicey, peppery and meaty aroma and taste nuances.

What is claimed is:

1. A process for augmenting or enhancing the aroma or taste of a smoking tobacco comprising the step of adding to said smoking tobacco an organoleptic property augmenting or enhancing quantity of a mixture of isobutyl substituted heterocyclic compounds having the generic formula:

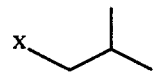

wherein X is a moiety selected from the group consisting of:

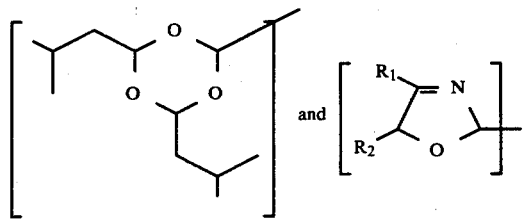

and wherein $R_1$ and $R_2$ are different and each is selected from the group consisting of methyl and ethyl, consisting of (i) 2,4,6-triisobutyl-1,3,5-trioxane having the formula:

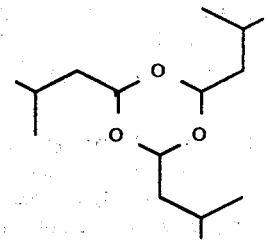

and (ii) a mixture of oxazoline compounds having the generic structure:

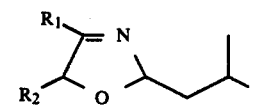

wherein $R_1$ and $R_2$ are different and each is selected from the group consisting of ethyl and methyl.

2. A smoking tobacco composition comprising smoking tobacco and intimately admixed therewith a composition useful in augmenting or enhancing the aroma or taste of said smoking tobacco consisting of (i) a smoking tobacco flavor augmenting or enhancing quantity of a mixture of isobutyl substituted heterocyclic compounds having the generic formula:

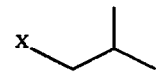

and wherein X is a moiety selected from the group consisting of:

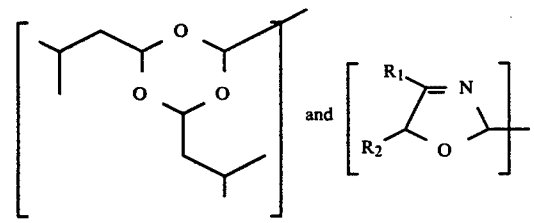

and wherein $R_1$ and $R_2$ are different and each is selected from the group consisting of methyl and ethyl, comprising (a) 2,4,6-triisobutyl-1,3,5-trioxane having the formula:

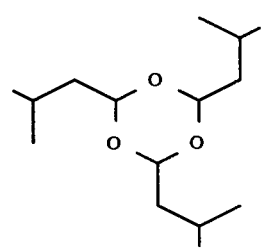

and (b) a mixture of oxazoline compounds having the generic structure:

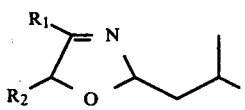

wherein $R_1$ and $R_2$ are different and each is selected from the group consisting of ethyl and methyl; and (ii) the remainder of said formulation being at least one adjuvant for said mixture being compatible with said mixture and said smoking tobacco and being selected from the group consisting of:

Beta-ethyl-cinnamaldehyde;
Eugenol;
Dipentene;
Damascenone;
Maltol;
Ethyl maltol;
Delta decalactone;
Benzaldehyde;
Amyl acetate;
Ethyl butyrate;
Ethyl valerate;
Ethyl acetate;
2-Hexenol-1;
2-Methyl-5-isopropyl-1,3-nonadiene-8-one;
2,6-Dimethyl-2,6-undecadiene-10-one;
2-Methyl-5-isopropyl acetophenone;
2-Hydroxy-2,5,5-8a-tetramethyl-1-(2-hydroxyethyl)-decahydronaphthalene;
Dodecahydro-3a,6,6-9a-tetramethyl naphtho(2,1b)-furan;
4-Hydroxy hexanoic acid, gamma lactone;
Polyisoprenoid hydrocarbons;
Celery seed oil;
Coffee extract;
Bergamot oil;
Cocoa extract;
Nutmeg oil; and
Origanum oil.

* * * * *